United States Patent [19]
Brewster

[11] Patent Number: 4,590,374
[45] Date of Patent: May 20, 1986

[54] INFRA-RED LIGHT ABSORPTION GAS DETECTOR

[75] Inventor: Arthur E. Brewster, Thaxted, United Kingdom

[73] Assignee: International Standard Electric Corporation, New York, N.Y.

[21] Appl. No.: 656,044

[22] Filed: Sep. 28, 1984

[30] Foreign Application Priority Data

Oct. 22, 1983 [GB] United Kingdom ................ 8328291

[51] Int. Cl.⁴ ........................ G01N 21/27; G02B 5/28
[52] U.S. Cl. ................................... 250/338; 250/339; 250/343; 350/1.6; 350/166
[58] Field of Search ................................ 350/166, 1.6; 250/338 GA, 339, 351, 343; 356/437, 436

[56] References Cited

U.S. PATENT DOCUMENTS 2,834,246  5/1958  Foskett et al. ...................... 356/418
3,940,623  2/1976  Hempowitz et al. ............... 250/343

*Primary Examiner*—Alfred E. Smith
*Assistant Examiner*—Constantine Hannaher
*Attorney, Agent, or Firm*—John T. O'Halloran

[57] ABSTRACT

A gas detector arrangement, e.g. for detecting carbon dioxide, includes an infra-red source, a photodetector and band pass filter disposed in the light path therebetween. The arrangement includes means for oscillating the pass-band of the filter across an absorption band edge of the gas to be detected. The arrangement is portable and may be installed in diving apparatus.

5 Claims, 3 Drawing Figures

INFRA-RED LIGHT ABSORPTION GAS DETECTOR

BACKGROUND OF THE INVENTION

This invention relates to arrangements for detecting gases and in particular for measuring carbon dioxide levels in breathing gas mixtures. The invention also relates to breathing apparatus, e.g. for underwater use.

It is desirable to monitor the composition of breathing gas mixtures to ensure that the concentration of carbon dioxide in the mixture remains below a predetermined maximum. This is particularly important in gas mixtures that are supplied to divers or other persons working under hostile conditions where the drowsiness induced by excessive carbon dioxide in the gas mixture could prove extremely dangerous.

A number of devices for detecting and measuring gases such as carbon dioxide are available. However, some of these devices are relatively expensive and none is sufficiently portable for monitoring in a breathing apparatus to provide remote sensing.

SUMMARY OF THE INVENTION

The object of the invention is to minimise or to overcome this disadvantage.

According to one aspect of the invention there is provided an arrangement for detecting and measuring the concentration of a gas having an infra-red absorption band, the arrangement including a light source and photodetector, a multilayer interference filter disposed in the light path between the source and detector, means for vibrating the filter such that its transmission peak oscillates across the absorption band edge of the gas to be detected.

According to another aspect of the invention there is provided an infra-red band pass interference filter assembly, including a laminar infra-red transparent body, a plurality of transparent dielectric layers of substantially equal thickness disposed on at least one surface of the body, and a supporting frame member within which the body is mounted via two or more resilient filaments whereby the body may be oscillated in a torsional mode.

Advantageously the filter comprises a silicon body provided with a series of surface layers to provide the desired characteristic. Such an arrangement is sufficiently compact to be mounted in a breathing apparatus to provide a load indication, e.g. of carbon dioxide levels to the wearer or to a remote station.

It is well known that certain gases, e.g. carbon dioxide, have distinctive absorption bands in the infra-red region of the spectrum. Thus absorption of infra-red radiation may be used to detect the presence of such a gas and may also provide a measure of its concentration. The arrangement described herein uses an oscillatory filter the pass-band of which is traversed across the edge of such an absorption band. This provides a continuous reference to provide compensation for changes in the output of the infra-red source. The technique also shows the use of a tuned amplifier to minimise the effect of background noise.

BRIEF DESCRIPTION OF THE DRAWING

An embodiment of the invention will now be described in which.

DETAILED DESCRIPTION OF THE PREFERRED EMBODIMENT

Figure 1:
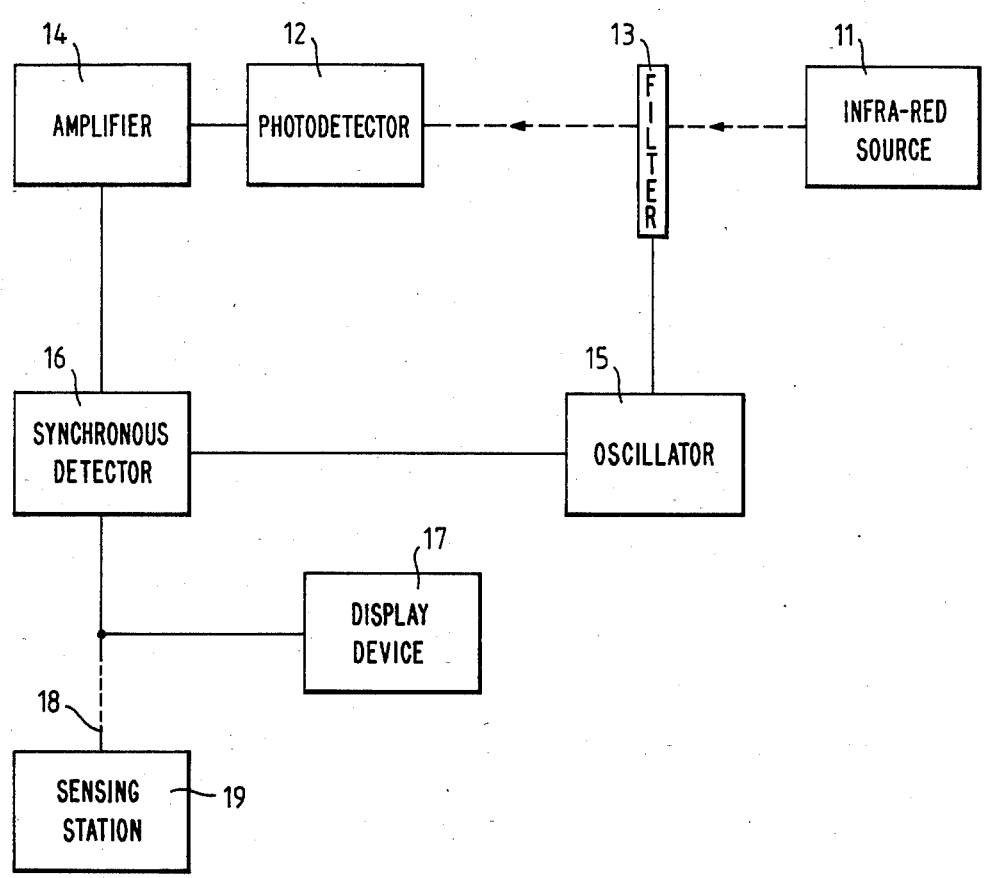
FIG. 1 is a schematic diagram of the gas detector.

Referring to the drawings, the gas detector arrangement includes an infra-red source 11, an associated photodetector 12 and a filter 13 disposed in the light path between the source and detector. Typically the infra-red source 11 comprises an electrically heated resistive filament, but other devices such as light emitting diode or a solid state laser can also be employed, provided they emit at the required wavelength. The output of the detector 12 is fed to an amplifier 14.

The filter 13 is maintained in oscillatory motion by an oscillator 15 whereby the filter transmission pass-band cut-off wavelength is varied at a frequency corresponding to the oscillator frequency. In the presence of a gas, e.g. carbon dioxide, having an absption band corresponding to the filter cut-off wavelength a corresponding oscillatory signal is produced by the detector 12. This signal is fed via the amplifier 14 to the signal input of a synchronous detector 16, the gate input of the detector 16 being coupled to the oscillator 15. This arrangement minimises the effect of background noise and also provides compensation for changes in the output of the source 11.

The output of the synchronous detector is fed to a band display device 17 and/or via a transmission line 18 to a remote sensing station 19.

Figure 2:
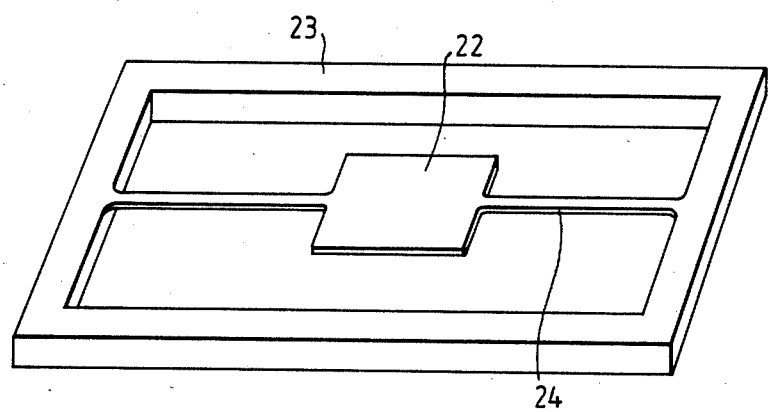
FIG. 2 shows one form of infra-red filter for use with the detector of FIG. 1; and, FIG. 3 illustrates the section of the filter of FIG. 2.
Figure 3:
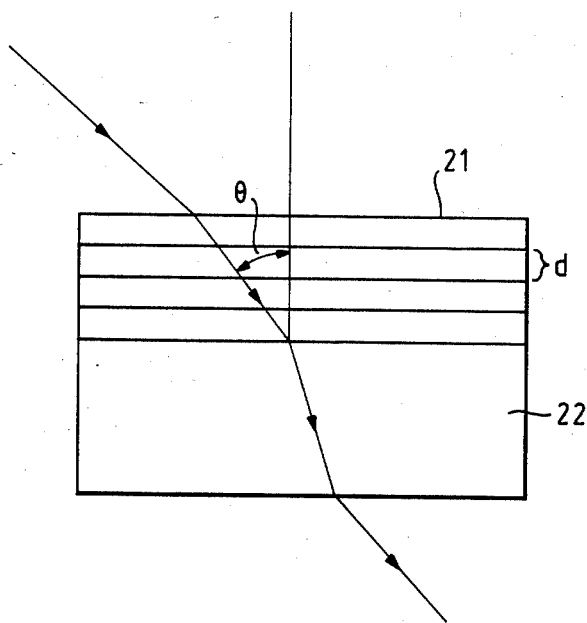

The filter which is shown in detail in FIGS. 2 and 3, is of the interference type and comprises a plurality of thin dielectric layers 21 of substantially equal thickness disposed on a supporting infra-red transparent body 22. Typically the supporting body 22 comprises a single crystal silicon structure that is formed by selective etching from a silicon wafer. Such a structure may comprise a frame 23 within which the body 22 is supported by filaments 23. Such a structure may be readily set into torsional oscillation, e.g. by electrostatic drive means (not shown).

The pass-band of the filter is determined by the thickness of the individual dielectric layers 21. These layers are of substantially equal thickness and, as is well known, are transmissive when the optical path length through each layer 21 is equal to an odd number of quarter wavelength. As can be seen from FIG. 3, rotation of the filter about an axis in its surface changes the aspect that is presented to an incident light beam. If d is the layer thickness then the path length 1 through each layer is given by $$l = d \sec \theta$$

where $\theta$ is the angle between the light beam and the normal at the filter surface.

By suitable choice of the layer thickness d the filter pass-band may be matched to an absption band of the gas to be detected such that, as the filter is oscillated, the pass-band is swept across the edge of the absption band to produce an amplitude modulated signal. For example, carbon dioxide gas has a significant absorption peak at a wavelength of 4.3 microns. By using a layer thickness d of 1 micron the filter characteristic can be matched to this absption peak to provide a measure of the concentration of the gas.

The gas detector is robust and portable and is particularly suitable for fitment to diving apparatus to provide a measure of carbon dioxide concentration to the wearer and/or via a wired connection to a surface monitoring station.

I claim:

1. An arrangement for detecting and measuring the concentration of a gas having an infra-red absorption band, the arrangement including a light source and photodetector, a multilayer interference filter disposed in the light path between the source and detector and supported on a single crystal silicon substrate, and means for vibrating the filter such that its transmission peak oscillates across the absorption band edge of the gas to be detected.

2. A gas detector arrangement as claimed in claim 1, wherein the substrate is suspended by a pair of integral resilient filaments in a frame support structure.

3. A gas detector arrangement as claimed in claim 1, and which includes a synchronous detector coupled via an amplifier to the photodetector and locked to the filter vibrational frequency.

4. A gas detector arrangement as claimed in claim 1, wherein said infra-red band pass interference filter includes an assembly including a laminar infra-red transparent body, a plurality of transparent dielectric layers of substantially equal thickness disposed on at least one surface of the body, and a supporting frame member within which the body is mounted via two or more resilent filaments whereby the body may be oscillated in a torsional mode.

5. A filter assembly as claimed in claim 4, wherein the body, support frame and filaments are formed by selective etching for a body of single crystal silicon.

* * * * *